(12) United States Patent
Seo et al.

(10) Patent No.: US 11,844,740 B2
(45) Date of Patent: *Dec. 19, 2023

(54) TORQUE PATTERN ADJUSTMENT APPARATUS AND METHOD FOR ADJUSTING TORQUE PATTERN USING THE SAME

(71) Applicant: Samsung Electronics Co., Ltd., Suwon-si (KR)

(72) Inventors: Keehong Seo, Seoul (KR); Byung-Kwon Choi, Seongnam-si (KR); Bokman Lim, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/184,281

(22) Filed: Mar. 15, 2023

(65) Prior Publication Data

US 2023/0218466 A1 Jul. 13, 2023

Related U.S. Application Data

(63) Continuation of application No. 16/585,756, filed on Sep. 27, 2019, now Pat. No. 11,628,117, which is a
(Continued)

(30) Foreign Application Priority Data

Sep. 1, 2014 (KR) .................. 10-2014-0115274

(51) Int. Cl.
*A61H 3/00* (2006.01)
*B25J 9/00* (2006.01)
(Continued)

(52) U.S. Cl.
CPC ............... *A61H 3/00* (2013.01); *A61B 5/112* (2013.01); *A61H 1/0262* (2013.01);
(Continued)

(58) Field of Classification Search
CPC ... A61H 3/00; A61H 1/00; A61H 1/02; A61H 1/0237; A61H 1/0274; A61H 1/0262;
(Continued)

(56) References Cited

U.S. PATENT DOCUMENTS

| 4,235,437 A | 11/1980 | Ruis et al. |
| 5,752,239 A | 5/1998 | Coutts |

(Continued)

FOREIGN PATENT DOCUMENTS

| JP | 3930399 B2 | 6/2007 |
| JP | 4255744 B2 | 4/2009 |

(Continued)

OTHER PUBLICATIONS

Korean Notice of Allowance dated Feb. 2, 2021 issued in corresponding Korean Patent Application No. 10-2014-0115274. English translation has been provided.

*Primary Examiner* — Tu A Vo
(74) *Attorney, Agent, or Firm* — Harness, Dickey & Pierce, P.L.C.

(57) ABSTRACT

An torque pattern adjustment apparatus including a display configured to display a first torque pattern corresponding to a gait cycle, and a generator configured to generate a second torque pattern by adjusting at least a portion of the first torque pattern in response to a reception of an input, and a torque pattern adjustment method using the same may be provided. The first torque pattern may be applied to a joint of a user.

18 Claims, 12 Drawing Sheets

Related U.S. Application Data continuation of application No. 14/610,731, filed on Jan. 30, 2015, now Pat. No. 10,548,799.

(51) Int. Cl.
*A61H 1/02* (2006.01)
*A61B 5/11* (2006.01)

(52) U.S. Cl.
CPC ....... *B25J 9/0006* (2013.01); *A61H 2003/007* (2013.01); *A61H 2201/165* (2013.01); *A61H 2201/1652* (2013.01); *A61H 2201/5043* (2013.01); *A61H 2201/5046* (2013.01); *A61H 2205/088* (2013.01); *A61H 2205/10* (2013.01)

(58) Field of Classification Search
CPC ........ A61H 2201/00; A61H 2201/0107; A61H 2201/0157; A61H 2201/5007; A61H 2201/501; A61H 2201/5023; A61H 2201/5025; A61H 2201/5035; A61H 2201/5038; A61H 2201/5043; A61H 2201/5046; A61H 2201/5058; A61H 2201/5064; A61H 2201/5066; A61H 2201/5069; A61H 2201/5097; B25J 9/0006

See application file for complete search history.

(56) References Cited

U.S. PATENT DOCUMENTS

| | | | |
|---|---|---|---|
| 5,931,763 A | 8/1999 | Alessandri | |
| 6,666,831 B1 | 12/2003 | Edgerton et al. | |
| 7,508,535 B2 | 3/2009 | Hart et al. | |
| 7,528,976 B2 | 5/2009 | Hart et al. | |
| 7,843,411 B2 | 11/2010 | Manning | |
| 2008/0255488 A1 | 10/2008 | Agrawal et al. | |
| 2009/0227925 A1* | 9/2009 | McBean | A61H 1/008 602/16 |
| 2010/0121232 A1 | 5/2010 | Sankai | |
| 2011/0071442 A1* | 3/2011 | Park | A61B 5/112 601/35 |
| 2011/0093089 A1 | 4/2011 | Martin | |
| 2012/0029399 A1 | 2/2012 | Sankai | |
| 2012/0172770 A1 | 7/2012 | Almesfer et al. | |
| 2012/0238920 A1 | 9/2012 | Schnapp et al. | |
| 2012/0259431 A1 | 10/2012 | Han et al. | |
| 2013/0158445 A1* | 6/2013 | Kazerooni | A61H 3/00 601/35 |
| 2014/0012164 A1* | 1/2014 | Tanaka | A61F 5/0125 601/35 |
| 2014/0075220 A1 | 3/2014 | Song | |
| 2014/0094721 A1 | 4/2014 | Diallo | |
| 2014/0171838 A1 | 6/2014 | Aleksov et al. | |
| 2014/0213951 A1 | 7/2014 | Pietrusisnki et al. | |
| 2016/0107309 A1 | 4/2016 | Walsh et al. | |
| 2016/0331625 A1* | 11/2016 | Sankai | A61H 3/00 |

FOREIGN PATENT DOCUMENTS

| | | |
|---|---|---|
| JP | 2010099418 A | 5/2010 |
| JP | 2012-045251 A | 3/2012 |
| JP | 5386253 B2 | 1/2014 |
| JP | 5505205 B2 | 5/2014 |
| JP | 2015-058033 A | 3/2015 |
| KR | 10-2012-0071555 A | 7/2012 |
| KR | 1361362 A | 8/2013 |
| KR | 20130101777 A | 9/2013 |
| KR | 10-2014-0001946 A | 1/2014 |
| KR | 10-2015-0077736 A | 7/2015 |

\* cited by examiner

TORQUE PATTERN ADJUSTMENT APPARATUS AND METHOD FOR ADJUSTING TORQUE PATTERN USING THE SAME

CROSS-REFERENCE TO RELATED APPLICATION

This application is a continuation of U.S. application Ser. No. 16/585,756, filed on Sep. 27, 2019, which is a continuation of U.S. application Ser. No. 14/610,731, filed on Jan. 30, 2015, now granted as U.S. Pat. No. 10,548,799 on Feb. 4, 2020, which claims priority under 35 U.S.C. § 119 to Korean Patent Application No. 10-2014-0115274, filed on Sep. 1, 2014, in the Korean Intellectual Property Office, the disclosure of each of which is incorporated herein by reference in its entirety.

BACKGROUND

1. Field

Some example embodiments relate to torque pattern adjustment apparatuses and/or methods, and more particularly, to methods and apparatuses for adjusting a pattern of a torque applied to a joint of a user and transmitting the adjusted pattern to a mobility aid apparatus.

2. Description of the Related Art

A user of a mobility aid apparatus generally determines an optimum mobility aid pattern through a decision of the user or an aid of an expert in a rehabilitation and medical field. Accordingly, methods and/or apparatuses which enable the user or the expert to provide the optimum mobility aid pattern by intuitively adjust a pattern of a torque or power applied to a joint of the user may be useful.

SUMMARY

At least one example embodiment relates to a torque pattern adjustment apparatus.

According to an example embodiment, a torque pattern adjustment apparatus includes a display configured to display a first torque pattern corresponding to a gait cycle and a generator configured to generate a second torque pattern by adjusting at least a portion of the first torque pattern in response to an input.

According to some example embodiments, the torque pattern adjustment apparatus may further include a transmitter configured to transmit the second torque pattern to an external apparatus. The external device may be one of a walking aid apparatus for providing a walking aid by applying the second torque pattern, and a rehabilitation aid apparatus for providing a rehabilitation aid by applying the second torque pattern.

According to some example embodiments, the first torque pattern may be set to be applied to a joint of a user According to some example embodiments, the generator may be configured to adjust at least one of an interval length of a peak, a position of the peak, and intensity of the peak, and an interval length of a base in the first torque pattern.

According to some example embodiments, the generator may be configured to set at least one adjustment point to the first torque pattern, and adjust a position of the at least one adjustment point based on the input.

According to some example embodiments, the generator may be configured to generate the second torque pattern based on the adjusted position of at least one adjustment point.

According to some example embodiments, the torque pattern adjustment apparatus may further include a storage configured to store first torque patterns respectively corresponding to walking conditions. The walking conditions may include at least one of a walking motion and a walking speed. The walking motion may include at least one of an ascending walking, a level walking, and a descending walking, and the walking speed may be classified into at least one speed level.

According to some example embodiments, the torque pattern adjustment apparatus may further include a setter configured to set on of the first torque patterns based on at least one other of the first torque pattern stored in the storage. The setter may be configured to set one of the first torque patterns based on an average value of the at least two other of the first torque patterns including the at least one other of the first torque patterns.

At least one example embodiment relates to a torque pattern adjustment method performed by a torque pattern adjustment apparatus.

According to an example embodiment, a torque pattern adjustment method includes displaying a first torque pattern corresponding to a gait cycle, receiving, through an input device, an input instructing an adjustment of the first torque pattern, and generating, using a processor, a second torque pattern by adjusting at least a portion of the first torque pattern based on the received input.

According to some example embodiments, the torque pattern adjustment method may further include transmitting the second torque pattern to an external apparatus. The external apparatus may be at least one of a walking aid apparatus for providing a walking aid by applying the second torque pattern, and a rehabilitation aid apparatus for providing a rehabilitation aid by applying the second torque pattern.

According to some example embodiments, the generating may include adjusting at least one of intensity of a peak, a position of the peak, and an interval length of the peak, and an interval length of a base in the first torque pattern.

According to some example embodiments, the generating may include setting at least one adjustment point to the first torque pattern, adjusting a position of the at least one adjustment point based on the input, and generating the second torque pattern based on the adjusted position of the at least one adjustment point.

According to some example embodiments, the torque pattern adjustment method may further include storing first torque patterns respectively corresponding to walking conditions, the walking conditions including at least one of a walking motion and a walking speed.

According to some example embodiments, the torque pattern adjustment method may further include performing a setting of one of the first torque patterns based on at least one other of the first torque patterns stored in a storage.

At least one example embodiment relates to an electronic apparatus

According to an example embodiment, an electronic apparatus includes a display screen configured to display a first graphical user interface (GUI) including a first torque pattern corresponding to a gait cycle, an input device configured to detect an input, a processor configured to enable the display screen to display, determine an input position on the display screen in response to the input received from the input device, and generate a second torque pattern by adjusting at least a portion of the first torque pattern. The electronic apparatus may further include a transmitter configured to transmit the second torque pattern to an external apparatus.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
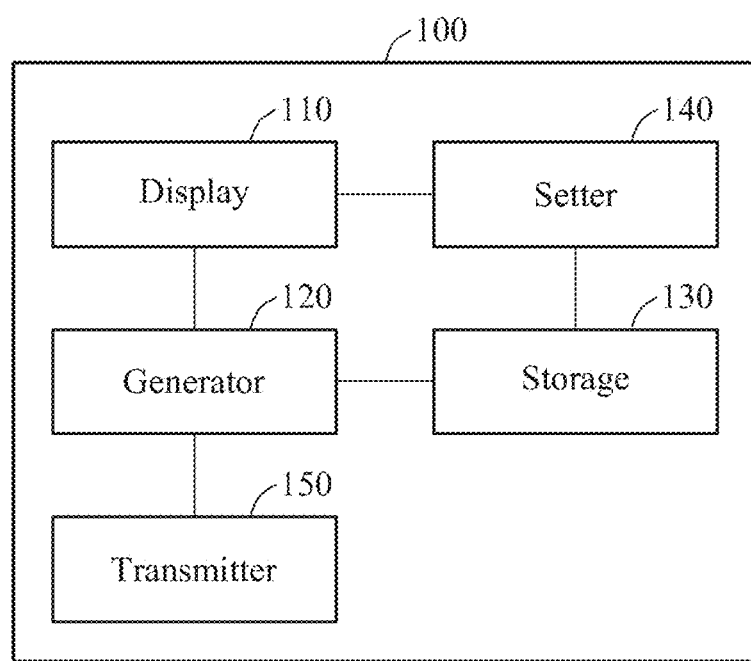
FIG. 1 is a block diagram illustrating a configuration of a torque pattern adjustment apparatus according to an example embodiment.

Some example embodiments now will be described more fully hereinafter with reference to the accompanying drawings. The example embodiments may, however, be embodied in many different forms and should not be construed as limited to the example embodiments set forth herein. Like reference numerals refer to like elements throughout.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. As used herein, the term "and/or" includes any and all combinations of one or more of the associated listed items. Expressions such as "at least one of," when preceding a list of elements, modify the entire list of elements and do not modify the individual elements of the list.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments. It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Meanwhile, when it is possible to implement any embodiment in any other way, a function or an operation specified in a specific block may be performed differently from a flow specified in a flowchart. For example, two consecutive blocks may actually perform the function or the operation simultaneously, and the two blocks may perform the function or the operation conversely according to a related operation or function.

Unless otherwise defined, all terms including technical and scientific terms used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

FIG. 1 is a block diagram illustrating a configuration of a torque pattern adjustment apparatus according to an example embodiment.

Referring to FIG. 1, a torque pattern adjustment apparatus 100 includes a display 110, a generator 120, a storage 130, a setter 140, and a transmitter 150.

The display 110 may display a first torque pattern corresponding to a gait cycle. The gait cycle may be set based on a single step of a user as a reference, and the first torque pattern may be set to correspond to each point in time of the gait cycle. The first torque pattern may be applied to a joint of the user participating a walking.

Hereinafter, the first torque pattern may refer to a torque pattern set to correspond to a walking condition stored in the storage 130, and a second torque pattern may refer to a torque pattern obtained by adjusting at least a portion of the first torque pattern.

The display 110 may display a graphical user interface (GUI) including the first torque pattern. Through this, the user may intuitively recognize the first torque pattern applied to the joint during walking, and intuitively adjust the first torque pattern.

The first torque pa set for respective joints used participating the walking, and/or may be set to correspond to respective walking conditions, which includes at least one of a walking motion and a walking speed. The first torque patterns corresponding to each walking condition may be stored in the storage 130.

Walking mechanisms of a body part (e.g., a hip joint) of a user may be different for respective walking motions, which includes, for example, an ascending walking (e.g., a walking slope-up), and a descending walking (e.g., a walking slope-down). Thus, the walking motion may include at least one of a level walking, the walking slope-up, and the walking slope-down, and the torque patterns may be set for respective walking motions. In the present disclosure, although the walking motion is described as including at least one of the level walking, the walking slope-up, and the walking slope-down for ease of description, the walking motions are not limited thereto. The walking motion may include more detailed motions, and may further include a motion using different a hip joint motion mechanism, for example, a standing state, a sitting-down state, and a standing-up state.

The walking speed may be classified into at least one speed level. Despite an identical walking motion, a torque pattern applied to the joint of the user may vary based on the walking speed. Thus, the walking speed may be used as a reference for setting the torque pattern.

At an initial stage, the first torque pattern(s) may be set based on an average value of a torque pattern corresponding to a common gait cycle. Further, torque patterns may be stored in the storage 130 and used as the first torque pattern(s).

The display 110 may display the first torque pattern stored in the storage 130 as a torque waveform to correspond to the gait cycle. Further, the display 110 may express intensity of a torque and/or a direction of the torque as an image for each joint of the user such that the user intuitively recognizes the intensity and the direction of the torque.

The generator 120 may generate a second torque pattern by adjusting at least a portion of the first torque pattern based on an input instructing an adjustment of the first torque pattern. The first torque pattern(s) may be adjusted to provide an optimized walking aid for the user.

The generator 120 may adjust the first torque pattern displayed on the display 110, based on the input instructing the adjustment of the first torque pattern, thereby generating the second torque pattern appropriate for the user. The generated second torque pattern may be stored in the storage 130.

The generator 120 may adjust at least one of a length of a base interval, a length of a peak interval, a position of the peak, and intensity of the peak in the first torque pattern. Thus, the user may adjust the first torque pattern to generate the second torque pattern optimized for the user.

The user may intuitively perform the adjustment of the first torque pattern displayed on the display 110, using an input from an input device. The input device may be, for example, a touch screen, a mouse, and a keyboard. The user may generate the second torque pattern by adjusting the first torque pattern displayed on the display 110 using the input from the input device.

The generator 120 may set at least one adjustment point in the first torque pattern to adjust the first torque pattern more precisely. The generator 120 may adjust a position of the at least one adjustment point based on an input of the user, and generate the second torque pattern based on the at least one adjusted adjustment point. A method of adjusting the first torque pattern in the generator 120 will be explained later.

The storage 130 may store the first torque pattern set in advance and the second torque pattern generated by adjusting the first torque pattern. The storage 130 may store the first torque pattern corresponding to each walking condition including at least one of the walking motion and the walking speed. When the second torque pattern is generated by adjusting the first torque pattern corresponding to a predetermined (or alternatively, desired) walking condition, the storage 130 may store the second torque pattern to correspond to the predetermined (or alternatively, desired) walking condition, and may also store the second torque pattern as a substitution of the first torque pattern corresponding to the predetermined (or alternatively, desired) walking condition. Thus, the user may store a torque pattern adjusted based on characteristics of the user in the storage 130 for each walking condition.

The setter 140 may set a new torque pattern based on the torque pattern stored in the storage 130. When the first torque pattern corresponding to at least one walking condition is not stored, the user may set the first torque pattern corresponding to the at least one walking condition. The setter 140 may automatically set a first torque pattern not stored in the storage 130 based on the first torque pattern for at least one other walking condition stored in the storage 130.

When a first torque pattern corresponding to a third walking condition is not stored, the setter 140 may set an average value of at least two other first torque patterns stored in the storage 130 as the first torque pattern corresponding to the third walking condition. For example, when the first torque pattern corresponding to the third walking condition is not stored, the setter 140 may set an average value of a first torque pattern corresponding to a first walking condition and a first torque pattern corresponding to a second walking condition as the first torque pattern corresponding to the third walking condition. Related descriptions will also be provided with reference to FIG. 10 later.

The display 110 may be a display screen included in, for example, a smartphone, a personal computer (PC), and a tablet PC to display the first torque pattern, and may be configured to be separate from the torque pattern adjustment apparatus 100. Wired or wireless communication may be performed between the display 110 and the torque pattern adjustment apparatus 100 when the display 110 is separately provided from the torque pattern adjustment apparatus 100. The generator 120 and the setter 140 may operate using respective configurations or using a single processor. The processor may enable the display screen to display a first GUI including a first torque pattern corresponding to the gait cycle.

An input instructing an adjustment of the first torque pattern may be received through the input device. The input device may detect the received input, and provide the input to the processor.

The processor may determine an input position in the display screen in response to the input from the input device, and generate the second torque pattern adjusting at least a portion of the first torque pattern. In response to the generating of the second torque pattern, the processor may enable the display screen to display a second GUI including the second torque pattern.

The transmitter 150 may transmit the second torque pattern generated in the generator 120 to an external apparatus. For example, the transmitter 150 may transmit the second torque pattern to a walking aid apparatus, and the walking aid apparatus may apply the second torque pattern to a walking condition corresponding to the received second torque pattern. Further, the transmitter 150 may transmit the second torque pattern to another torque pattern adjustment apparatus, and the another torque pattern adjustment apparatus may verify the adjusted second torque pattern.

The walking aid apparatus is described as an example of the external apparatus to which the second torque pattern is transmitted by the transmitter 150. However, the disclosure is not limited thereto. The second torque pattern may be transmitted to, for example, a rehabilitation aid apparatus for providing a rehabilitation aid, a torque pattern adjustment apparatus, and/or an electronic apparatus for monitoring the second torque pattern (e.g., a PC, a smartphone, a tablet PC).

When the second torque pattern is transmitted to the rehabilitation aid apparatus, the rehabilitation apparatus may provide an appropriate walking aid to the user by applying the second torque pattern. When the second torque pattern is transmitted to the torque pattern adjustment apparatus, the second torque pattern, which is generated by adjusting the first torque pattern, may be monitored and readjusted by verifying whether the second torque pattern is optimized for the user. Further, the second torque pattern may be monitored when the electronic apparatus (e.g., PC, the smartphone, tablet PC) received the second torque pattern.

The torque pattern adjustment apparatus 100 of FIG. 1 relates to a hip-type walking aid apparatus, a type of a walking aid apparatus is not limited thereto. The present disclosure may be applicable to a walking aid apparatus that supports an entire lower limb, or a walking aid apparatus that supports a portion of a lower limb. The present disclosure may also be applicable to all types of walking aid apparatuses for providing a walking aid, for example, a walking aid apparatus that supports down to a knee, and a walking assistance apparatus that supports down to an ankle. It would be obvious to those skilled in the art that the present disclosure is also applicable to an apparatus for providing a rehabilitation aid to a user.

Figure 2:
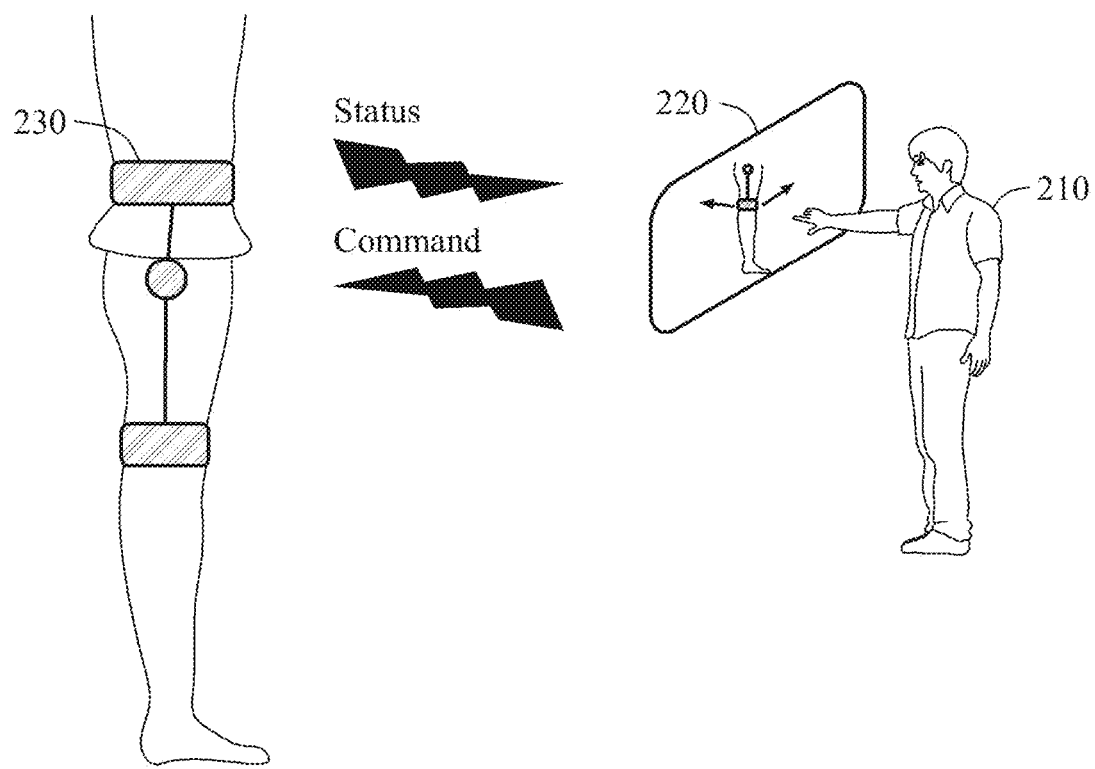
FIG. 2 is a diagram illustrating a torque pattern adjustment method according to an example embodiment.

FIG. 2 is a diagram illustrating a torque pattern adjustment method according to an example embodiment.

Referring to FIG. 2, a user 210 may adjust the torque pattern applied to a joint of the user 210 during walking using a torque pattern adjustment apparatus 220.

The torque pattern adjustment apparatus 220 may display a GUI including the torque pattern for the user 210 to intuitively adjust the torque pattern. Thus, the user 210 may intuitively adjust the torque pattern applied to the joint of the user 210.

The user 210 adjusting the torque pattern through the torque pattern adjustment apparatus 220 may be a third party, who is not wearing a walking aid apparatus, and/or a user wearing the walking aid apparatus. The third party may be, for example, a medical expert, a rehabilitation expert, and an assistant assisting the user wearing the walking aid apparatus.

The torque pattern adjusted in the torque pattern adjustment apparatus 220 may be transmitted to a walking aid apparatus 230. The walking aid apparatus 230 may receive the adjusted torque pattern and apply the adjusted torque pattern to a walking condition corresponding to the adjusted torque pattern. Thus, a user may be provided with an efficient walking aid by applying the adjusted or optimized torque pattern.

Also, the walking aid apparatus 230 may transmit a state of operation according to a set torque pattern to the torque pattern adjustment apparatus 220. Based on the state received from the walking aid apparatus 230, the torque pattern adjustment apparatus 220 may verify whether the currently set torque pattern is appropriate for the user, and/or adjust the torque pattern based on a result of the verification.

The torque pattern adjustment apparatus 220 may remotely adjust the torque pattern and transmit the adjusted torque pattern to the walking aid apparatus 230 such that the adjusted torque pattern is applied. Thus, the torque pattern adjustment apparatus 220 may set a torque pattern appropriate for the user in real time, and provide the torque pattern to the walking aid apparatus 230.

Figure 3:
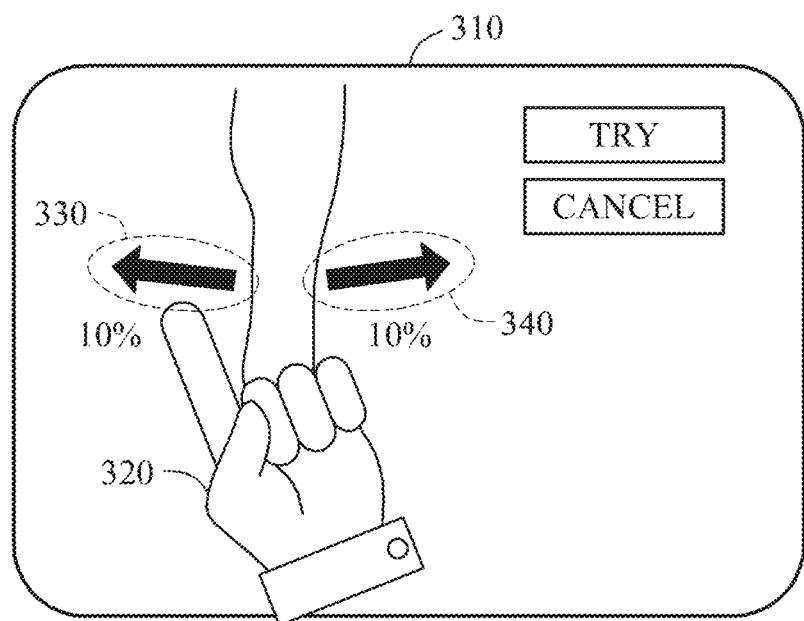
FIG. 3 is a diagram illustrating a method of adjusting intensity and a direction of a torque pattern according to an example embodiment.

FIG. 3 is a diagram illustrating a method of adjusting intensity and a direction of a torque pattern according to an example embodiment.

Referring to FIG. 3, a user may adjust a first torque pattern set to be applied to, for example, a hip joint of the user using a torque pattern adjustment apparatus 310. The first torque pattern may be displayed as a torque corresponding to a hip joint rotating direction and intensity of the torque so that the first torque pattern is intuitively recognized by the user.

The torque pattern adjustment apparatus 310 may display the hip joint rotating directions using arrows 330 and 340, and indicate the intensity of the torque applied corresponding to each direction through a digitization. Thus, the user may intuitively recognize the first torque pattern applied to the hip joint.

In an example, the user may adjust the intensity of the torque applied to the hip joint by touching and dragging the arrows 330 and 340 indicating hip joint rotating directions and displayed on the torque pattern adjustment apparatus 310.

For example, the user's input 320 may select the arrow 330 indicating a direction in which a lower limb moves backward. When the user provides the input 320, selects the arrow 330, and drags the arrow 330 in a same direction to the direction indicated by the arrow 330, intensity of a torque corresponding to the direction in which the lower limb moves backward may increase. In contrast, when the user provide the input 320, select the arrow 330, and drags the arrow 330 in an opposite direction to the direction indicated by the arrow 330, the intensity of the torque corresponding to the direction in which the lower limb moves backward may decrease.

As such, the user may generate a second torque pattern appropriate for the user to intuitively recognize and adjust the first torque pattern displayed on the torque pattern adjustment apparatus 310.

Although an input instructing an adjustment of the first torque pattern is described based on a touch input in the preceding and following examples, a type of a user input is not limited thereto. The user input may receive from an input device, for example, a mouse input, a keyboard input, or a gesture input.

Figure 4:
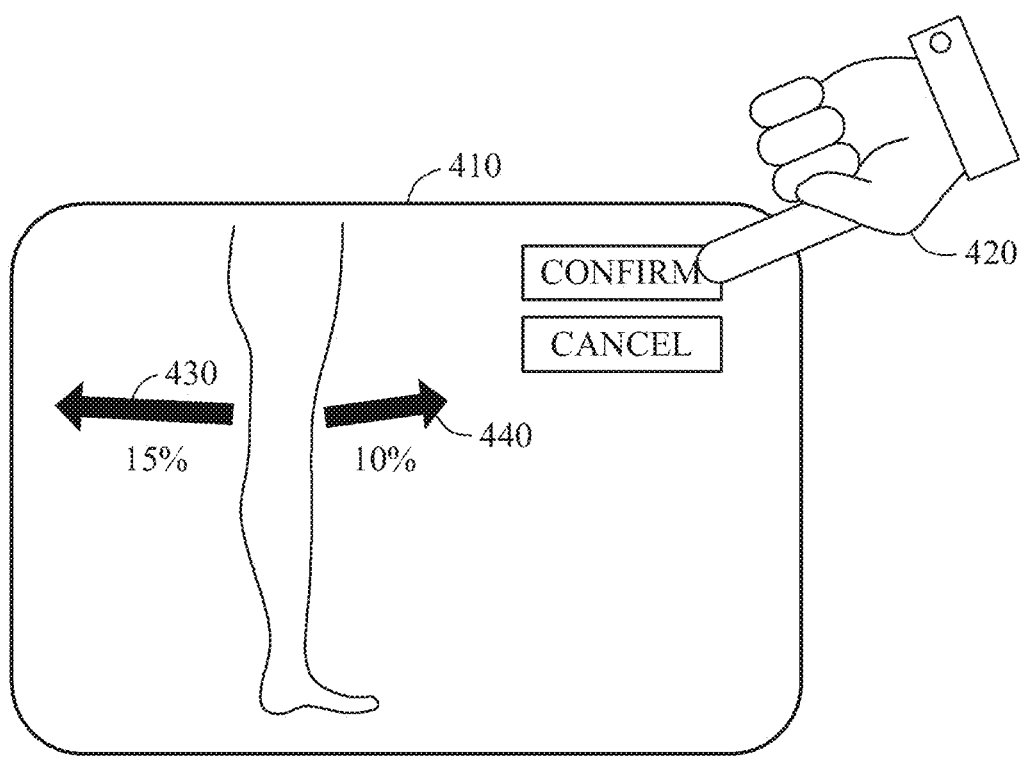
FIG. 4 is a diagram illustrating a method of determining intensity and a direction of the torque pattern adjusted in FIG. 3, according to an example embodiment.

FIG. 4 is a diagram illustrating a method of determining intensity and a direction of the torque pattern adjusted in FIG. 3, according to an example embodiment.

Referring to FIG. 4, a user may verify the intensity and the direction of the torque pattern adjusted in FIG. 3, and may generate a second torque pattern through an adjustment using a torque pattern adjustment apparatus 410.

When intensity of a torque in a direction 430 in which a lower limb moves backward is adjusted from 10% to 15%, the torque pattern adjustment apparatus 410 may provide the second torque pattern, which is obtained by adjusting a first torque pattern set to be applied to the user, before adjusting the intensity of the torque to 15%. Intensity of a torque in a direction 440 in which the lower limb moves forward may be displayed and provided to the user. In this example, the intensity of the torque in the direction 440 may not be adjusted.

Thus, the user may verify the second torque pattern, which is obtained by adjusting a first torque pattern set to be applied to, for example, a hip joint of the user, and generate the second torque pattern based on an input 420.

Although the descriptions of FIGS. 3 and 4 is provided based on the torque pattern applied to the hip joint of the user for ease of description, the torque pattern is not limited thereto. It would be obvious to those skilled in the art that the user may adjust a torque pattern applied to, for example, a knee joint and an ankle joint used for a walking motion.

Figure 5:
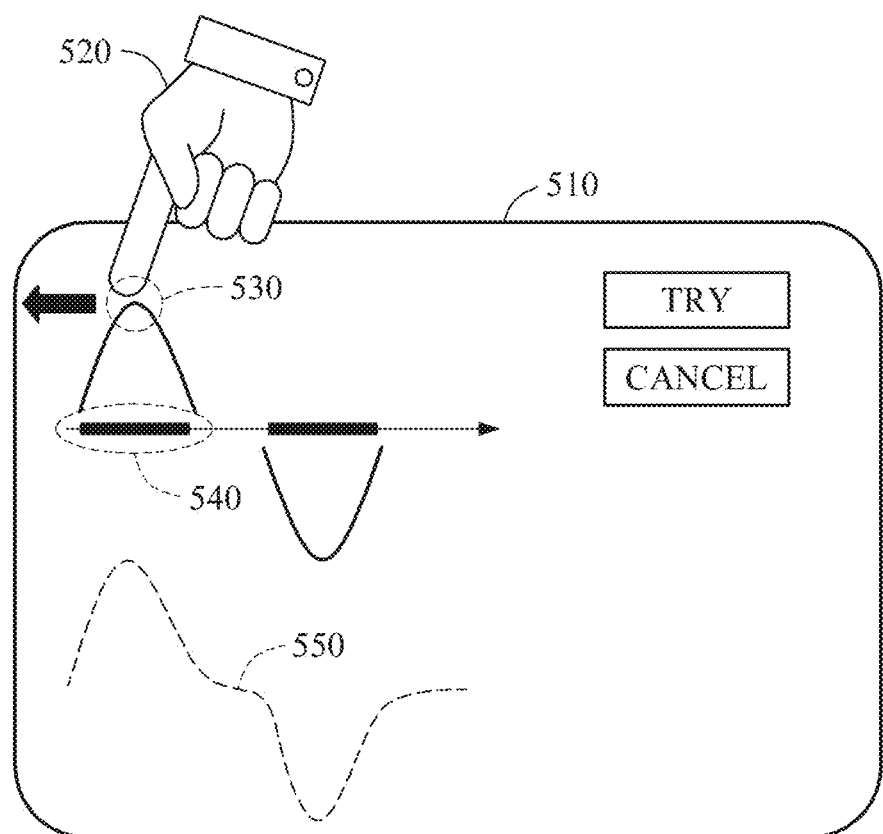
FIG. 5 is a diagram illustrating a method of adjusting intensity and a position of a peak and a position of a base in a torque pattern according to an example embodiment.

FIG. 5 is a diagram illustrating a method of adjusting intensity and a position of a peak and a position of a base in a torque pattern according to an example embodiment.

FIG. 5 illustrates a method of adjusting intensity and a position of a peak and a position of a base in a first torque pattern corresponding to a gait cycle in a torque pattern adjustment apparatus 510. The torque pattern adjustment apparatus 510 may display the first torque pattern set to be applied to a joint of a user using a display.

As illustrated in FIG. 5, the first torque pattern may be indicated as a waveform of a torque that corresponds to each point in time of the gait cycle. Accordingly, the user may intuitively recognize the first torque pattern applied to the joint during the gait cycle.

The user may adjust, based on an input 520, intensity and a position of a peak 530 and a position (or an interval) of base 540 in the first torque pattern based on a walking type of the user. For example, the user may touch a portion of the peak 530 in the first torque pattern displayed on the torque pattern adjustment apparatus 510. The user may touch the portion of the peak 530 in the first torque pattern and drag the portion in a desired direction. Thus, the position of the peak 530 in the first torque pattern may be moved to a position at which a drag of the input 520 ends. The position of the peak 530 in the torque pattern may be moved within the interval of the base 540.

Similarly, the user may touch a portion of the base in the first torque pattern, and drag the portion in a desired direction. Thus, the position of the base 540 in the first torque pattern may be moved to a position at which a drag of the input 520 ends.

Further, the user may touch the portion of the peak 530, and drag the portion in an upward direction to increase the intensity of the peak 530. Thus, the position of the peak 530 in the first torque pattern may be moved upwards to a position at which a drag of the input 520 ends.

Conversely, the user may touch the portion of the peak 530, and drag the portion in a downward direction to decrease the intensity of the peak 530. Thus, the position of the peak 530 in the first torque pattern may be moved downwards to a position at which a drag of the input 520 ends.

As described above, the user may intuitively recognize the first torque pattern displayed on the torque pattern adjustment apparatus 510 and adjust the intensity of the peak 530, the position of the peak 530, and/or the position of the base 540 in the first torque pattern, thereby generating the second torque pattern appropriate for the user.

Further, the torque pattern adjustment apparatus 510 may provide a second torque pattern 550 generated by adjusting, for example, the intensity and the position of the peak 530 and the position of the base 540 in the first torque pattern based on the input 520, to the user, virtually in real time. The user may recognize the second torque pattern 550 in real time during a process of adjusting the peak 530 and the base 540 of the first torque pattern based on the input 520, thereby generating a torque pattern optimized to the user.

Figure 6:
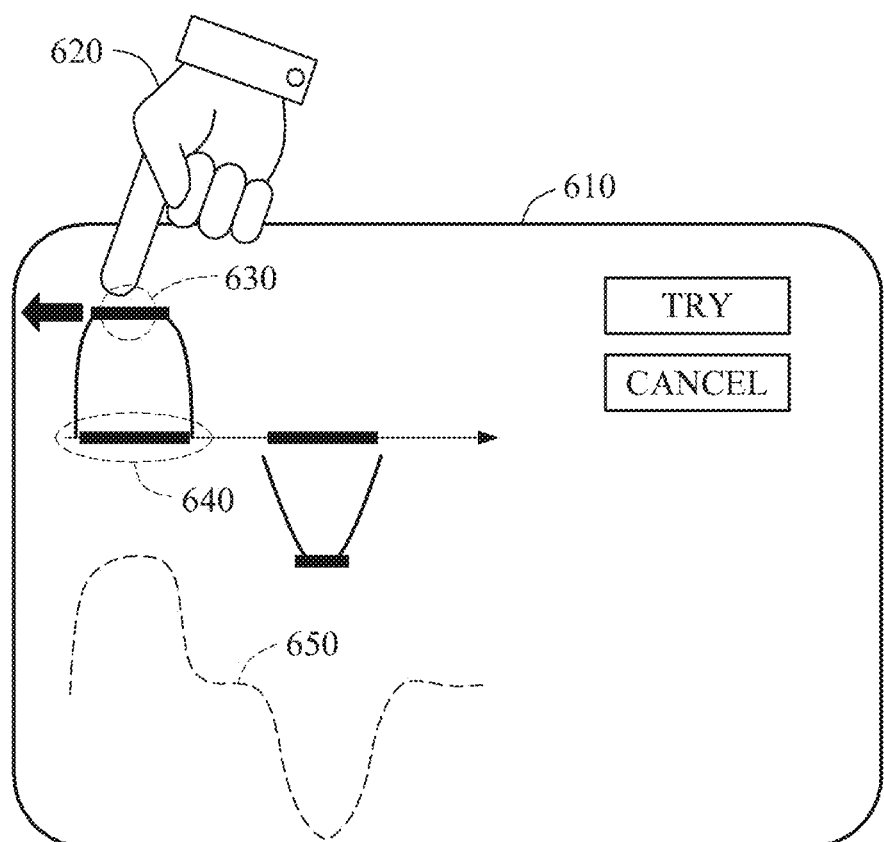
FIG. 6 is a diagram illustrating a method of adjusting a length of a base interval and a length of a peak interval in a torque pattern according to an example embodiment.

FIG. 6 is a diagram illustrating a method of adjusting an interval length of a peak and an interval length of a base in a torque pattern according to an example embodiment.

FIG. 6 illustrates a method of adjusting an interval length of a peak 630 and the interval length of base 640 in a first torque pattern corresponding to a gait cycle in a torque pattern adjustment apparatus 610. The torque pattern adjustment apparatus 610 may display the first torque pattern set to be applied to a joint of a user using a display.

As illustrated in FIG. 5, the first torque pattern may be indicated as a waveform of a torque that corresponds to each point in time of a gait cycle. Thus, the user may intuitively recognize the first torque pattern applied to the joint during the gait cycle.

The user may adjust the interval length of the peak 630 and the interval length of the base 640 in the first torque pattern through an input 620 according to a walking type of the user. For example, the user may touch at least two points in a portion of the peak 630 in the first torque pattern. To increase the interval length of the peak 630 in the first torque pattern, the user may increase a distance between the two touched points such that the interval length of the peak 630 is increased by a distance between two points at which the two touched points end.

Conversely, to reduce the interval length of the peak 630 in the first torque pattern, the user may reduce the distance between the two touched points such that the interval length of the peak 630 is reduced by the distance between two points at which the two touched points end.

The interval length of the base 640 in the first torque pattern may be adjusted using a same or similar method to the method of adjusting the interval length of the peak 630 described above. Further, the user may remove the peak 630 or generate a new peak in the first torque pattern by, for example, making a long touch on the portion of the peak 630 in the first torque pattern.

As described above, the user may intuitively recognize the first torque pattern displayed on the torque pattern adjustment apparatus 610 and adjust the interval length of the peak 630 and the interval length of the base 640, thereby generating the second torque pattern appropriate for the user.

Further, the torque pattern adjustment apparatus 610 may generate a second torque pattern 650 generated by adjusting the interval length of the peak 630 and the interval length of the base 640 in the first torque pattern based on the input 620, and provide to the user, for example, in real time. The user may recognize the second torque pattern 650 in real time during a process of adjusting the peak 630 and the base 640 through the input 620, thereby generating a torque pattern optimized to the user.

Figure 7:
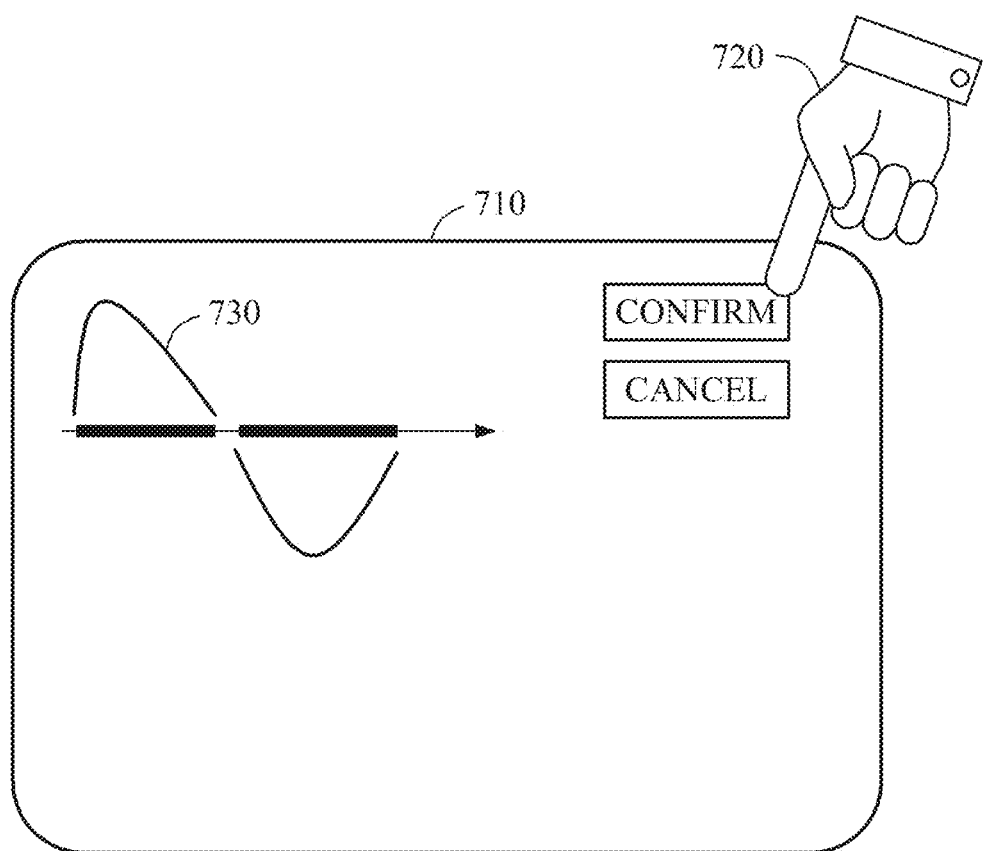
FIG. 7 is a diagram illustrating a method of determining the torque pattern adjusted in FIG. 5 or FIG. 6, according to an example embodiment.

FIG. 7 is a diagram illustrating a method of determining the torque pattern adjusted in FIG. 5 or FIG. 6, according to an example embodiment.

Referring to FIG. 7, a user may verify the position and the interval length of the peak, and the position and the interval length of the base adjusted in the examples illustrated in FIG. 5 or 6, thereby generating the second torque pattern 730, which is obtained by adjusting the first torque pattern, using a torque pattern adjusting apparatus 710.

As illustrated in FIG. 7, when a position of a peak of the first torque pattern is adjusted, a second torque pattern may be provided to the user before generating the second torque pattern, which is obtained by adjusting the position of the peak of the first torque pattern.

Accordingly, the user may verify the second torque pattern, which is obtained by adjusting the position of the peak of the first torque pattern, corresponding to a gait cycle, and generate the second torque pattern in response to a confirmation input 720.

Figure 8:
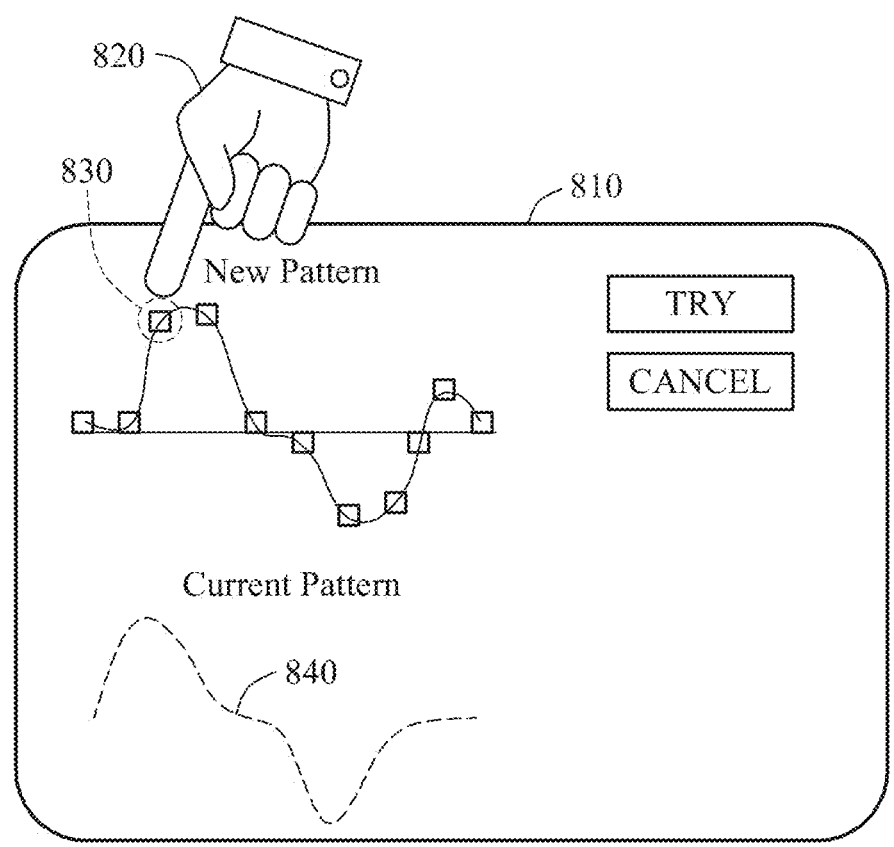
FIG. 8 is a diagram illustrating a method of adjusting a position of an adjustment point, which is set on a torque pattern, according to an example embodiment.

FIG. 8 is a diagram illustrating a method of adjusting a position of an adjustment point, which is set on a torque pattern according to an example embodiment.

Referring to FIG. 8, a torque pattern adjustment apparatus 810 may set at least one adjustment point 830 on a first torque pattern corresponding to a gait cycle so as to more precisely adjust the first torque pattern. Adjustment points may be vertically disposed at an equal horizontal interval. The user may adjust a vertical height for each of the adjustment points based on an input 820.

The torque pattern adjustment apparatus 810 may generate a second torque pattern by connecting the adjusted adjustment points to form a spline. Thus, the user may generate the second torque pattern by more precisely adjusting the first torque pattern.

At this time, the torque pattern adjustment apparatus 810 may provide a first torque pattern 840, which is currently set. The user may compare the first torque pattern 840 and a second torque pattern generated by adjusting a vertical height of at least one adjustment point 830 set on the first torque pattern. The user may generate a torque pattern optimized to the user by comparing in real time the first torque pattern 840 and the second torque pattern during a process of adjusting the vertical height.

Although the descriptions about the method of adjusting the first torque pattern is provided with reference of FIGS. 5 through 8 for ease of description, the disclosure is not limited thereto. The first torque pattern corresponding to the gait cycle and displayed on the torque pattern adjustment apparatus may be diversely adjusted to provide an optimized walking aid to the user based on an user input for, for example, changing a waveform of the first torque pattern or based on an user input of a new waveform based on the walking type of the user.

Figure 9:
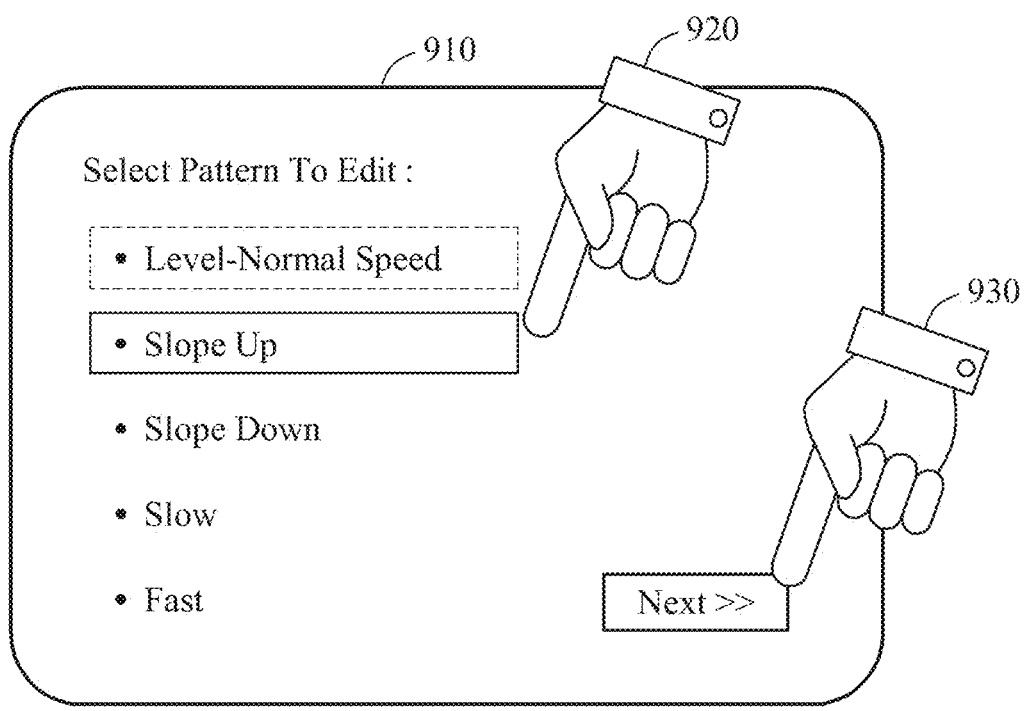
FIG. 9 is a diagram illustrating a method of selecting a torque pattern corresponding to one of the walking conditions, which include at least one of a walking motion and a walking speed, according to an example embodiment.

FIG. 9 is a diagram illustrating a method of selecting a torque pattern corresponding to one of the walking conditions, which include at least one of a walking motion and a walking speed according to an example embodiment.

A first torque pattern set to be applied to a joint of a user during walking may be set for each walking condition, which includes at least one of a walking motion and a walking speed.

As described above, a walking may have a different joint motion mechanism for each walking motion. Although the walking motions are identical to each other, a torque pattern applied to the joint may vary based on the walking speed. Thus, the first torque pattern may be set based on at least one of the walking motion and the walking speed.

When the first torque pattern is to be adjusted in a torque pattern adjustment apparatus 910, the user may select at least one of the walking motion and the walking speed. The selecting may be performed based on the foregoing cases in each of which the first torque pattern is set based on at least one of the walking motion and the walking speed.

When the torque pattern adjustment apparatus 910 automatically recognizes a walking condition including, for example, at least one of a terrain in which a user wearing a walking aid apparatus is currently located and a walking speed of the user, the torque pattern adjustment apparatus 910 may display the a first torque pattern corresponding to the walking condition currently being recognized.

When the torque pattern adjustment apparatus 910 fails to automatically recognize the walking condition including, for example, at least one of the terrain in which the user wearing a walking aid apparatus is currently located and the walking speed of the user, the user may select a walking condition and display a first torque pattern corresponding to the selected walking condition.

The user may select, for example, at least one of the walking motion and the walking speed through an input 920. The walking condition may be classified based on, for example, at least one of the walking motion and the walking speed, or classified by combining the walking motion and the walking speed.

For example, the walking condition may be classified into, for example, a walking slope-up, a walking slope-down, a level walking, a normal speed walking, a fast walking, and a slow walking. Although walking motions are identical to each other, the walking conditions with respect to the identical walking motions may be differently classified into, for example, the walking slope-up—the fast walking, the walking slope-up—the normal speed walking, and the walking slope-up—the slow walking, based on the walking speed.

The user may perform the input 920 to select the walking condition corresponding to the first torque pattern to be adjusted, and then, perform an input 930 to proceed to an operation of adjusting the first torque pattern.

Figure 10:
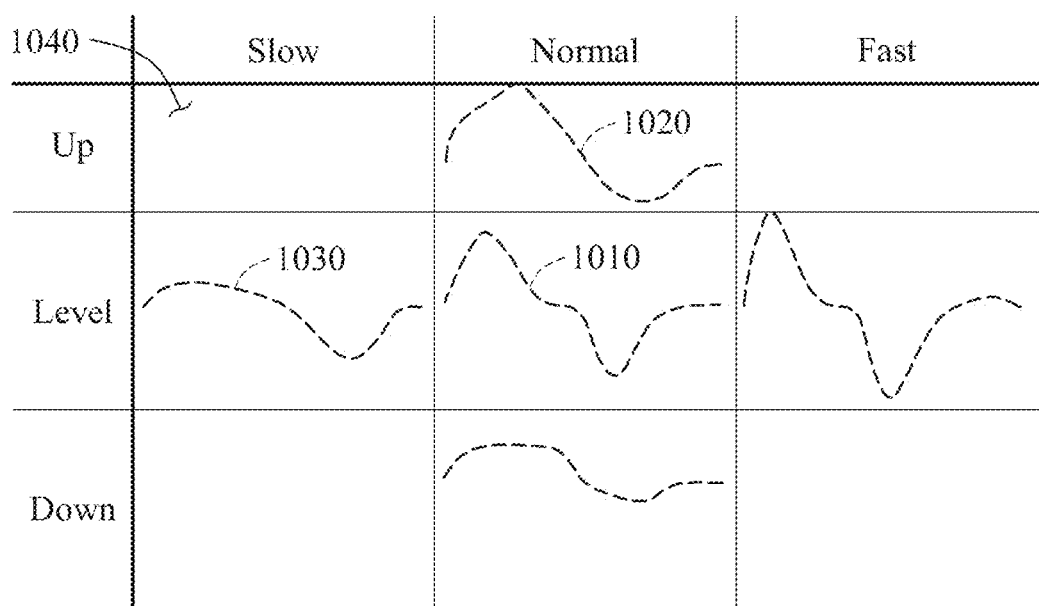
FIG. 10 is a diagram illustrating a method of setting an unstored torque pattern corresponding to one walking condition based on at least one stored torque pattern corresponding to at least one other walking condition, according to an example embodiment.

FIG. 10 is a diagram illustrating a method of setting an unstored torque pattern corresponding to one walking condition based on at least one stored torque pattern corresponding to at least one other walking condition, according to an example embodiment.

FIG. 10 illustrates a method of automatically setting an unstored torque pattern corresponding to one walking condition based on a first torque pattern or first torque patterns stored in advance and corresponding to one or more other walking conditions. This method may be useful when a first torque pattern corresponding to at least one of walking conditions is not stored in a torque pattern adjustment apparatus.

When a first torque pattern corresponding to a walking condition is not stored, a user may set the first torque pattern corresponding to the walking condition using a torque pattern adjustment apparatus. The torque pattern adjustment apparatus may automatically set the first torque pattern, which is not stored in the torque pattern adjustment apparatus and corresponding to one walking condition, based on other first torque pattern(s), which is/are stored in the torque pattern adjustment apparatus and corresponding other walking condition(s) instead of a case in which the user sets a torque pattern for each walking condition.

In a table of FIG. 10, a column represents a walking motion classified into, for example, a walking slope-up, a walking slope-down, and a level walking. A row represents a walking speed classified into, for example, a slow walking, a normal speed walking, and a fast walking.

FIG. 10 includes dotted curves, each indicating a first torque pattern stored in the storage 130 for each walking condition. For example, a first torque pattern 1010 may be a first torque pattern corresponding to the level walking—the normal speed walking. FIG. 10 includes blanks, each of which indicates that a first torque pattern is not stored in the storage 130 for a corresponding walking condition.

As described above, the first torque pattern not stored in the storage 130 may be automatically set based on the first torque pattern stored in the storage 130. For example, a first torque pattern corresponding to the walking slope-up—the slow walking may not be currently stored in the torque pattern adjustment apparatus as indicated by a blank 1040.

The first torque pattern corresponding to the walking slope-up—the slow walking may be set based on a first torque pattern 1020 corresponding to the walking slope-up—the normal speed walking and a first torque pattern 1030 corresponding to the level walking—the slow walking.

The first torque pattern corresponding to the walking slope-up—the slow walking may be one of walking conditions of the first torque pattern 1020 corresponding to the walking slope-up—the normal speed walking and the first torque pattern 1030 corresponding to the level walking—the slow walking.

For example, a walking motion of the first torque pattern corresponding to the walking slope-up—the slow walking may match a walking motion of the first torque pattern 1020 corresponding to the walking slope-up—the normal speed walking, or a walking speed of the first torque pattern corresponding to the walking slope-up—the slow walking may match the walking speed of the first torque pattern 1030 corresponding to the level walking—the slow walking.

As such, when the walking condition includes at least one of the walking motion and the walking speed, the first torque pattern, which is not stored in the torque pattern adjustment apparatus and corresponding to one walking condition, may be generated based on a first torque pattern, which is stored in the torque pattern adjustment apparatus and corresponding to the other walking condition and one of walking conditions of which matches one of the walking conditions of the first torque pattern not stored in the torque pattern adjustment apparatus.

For example, a relationship between the first torque pattern 1010 corresponding to the level walking—the normal speed walking and the first torque pattern 1020 corresponding to the walking slope-up—the normal speed walking may be acquired based on the walking conditions. Further, a relationship between the first torque pattern 1010 corresponding to the level walking—the normal speed walking and the first torque pattern 1030 corresponding to the level walking—the slow walking may be acquired based on the walking conditions.

The first torque pattern corresponding to the walking slope-up—the slow walking may be determined based on these two relationships.

The first torque pattern corresponding to the walking slope-up—the slow walking may be determined based on an average value of the first torque pattern 1020 corresponding to the walking slope-up—the normal speed walking and the first torque pattern 1030 corresponding to the level walking—the slow walking.

Accordingly, the first torque pattern corresponding to the walking conditions not stored in the storage 130 may be automatically set and stored in the storage although the user does not set the first torque pattern through the setter 140.

Figure 11:
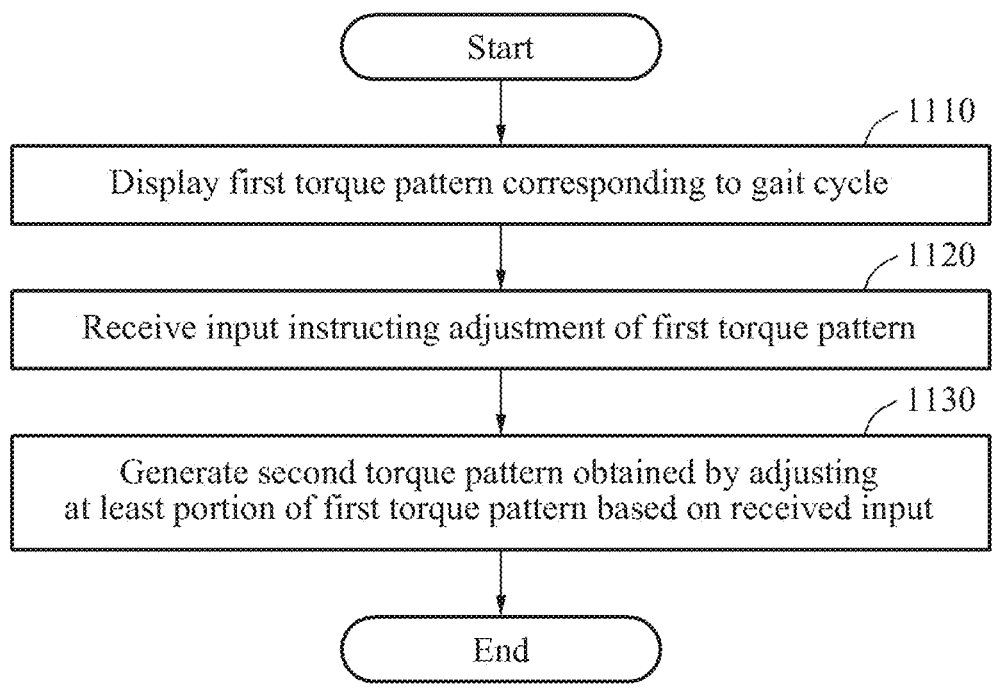
FIG. 11 is a flowchart illustrating a method of generating a second torque pattern by adjusting at least a portion of a first torque pattern, according to an example embodiment.

FIG. 11 is a flowchart illustrating a method of generating a second torque pattern by adjusting at least a portion of a first torque pattern, according to an example embodiment.

In operation 1110, the display 110 displays a first torque pattern corresponding to a gait cycle. Thus, a user may intuitively recognize the first torque pattern applied to a joint during walking, and perform an input instructing an adjustment of the first torque pattern.

The first torque pattern may be differently set for each joint used for walking, and set to correspond to each walking condition including, for example, at least one of a walking motion and a walking speed. The first torque pattern corresponding to each walking condition may be stored in the storage 130.

In operation 1120, the input instructing the adjustment of the first torque pattern is received through an input device. The user may use the input device, for example, a touch panel, a mouse, and a keyboard to instruct the adjustment of the first torque pattern to be appropriated for the user.

In operation 1130, the generator 120 generates a second torque pattern obtained by adjusting at least a portion of the first torque pattern based on the input instructing the adjustment of the first torque pattern. The generator 120 may adjust the first torque pattern displayed on the display 120 based on the input instructing the adjustment of the first torque pattern, thereby generating the second torque pattern appropriate for the user. The generated second torque pattern may be stored in the storage 130, for example, replacing the first torque pattern.

The generator 120 may adjust, for example, at least one of an interval length of a base, and intensity, a position, and an interval length of a peak in the first torque pattern. Thus, the user may adjust the first torque pattern to the second torque pattern, which is optimized for the user.

The generator 120 may set at least one adjustment point to the first torque pattern to more precisely adjust the first torque pattern. The generator 120 may adjust a position of the adjustment point, and generate the second torque pattern based on the adjusted adjustment point.

Figure 12:
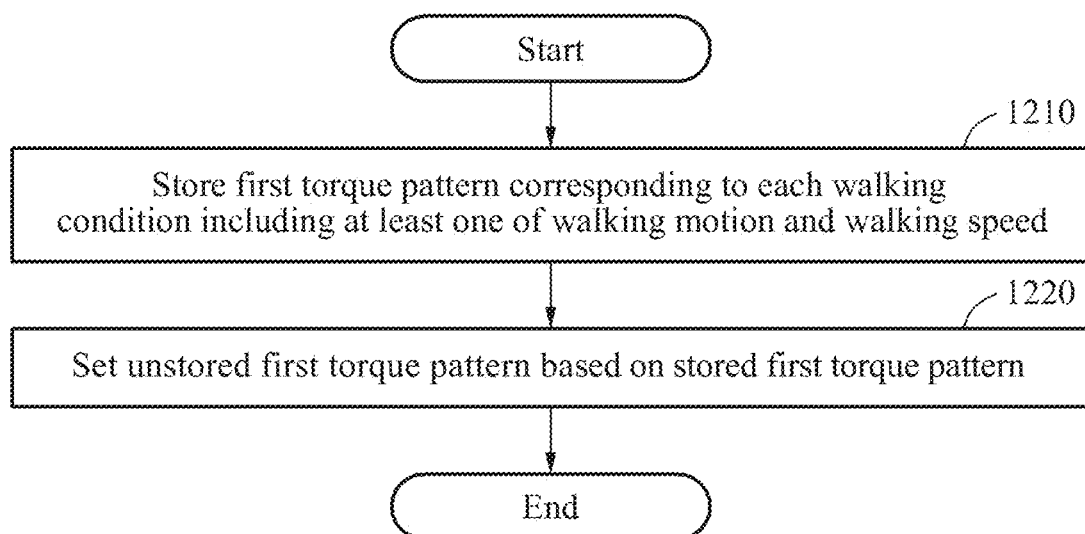
FIG. 12 is a flowchart illustrating a method of setting an unstored torque pattern corresponding to one walking condition based on at least one stored torque pattern corresponding to at least one other walking condition, according to an example embodiment.

FIG. 12 is a flowchart illustrating a method of setting an unstored torque pattern corresponding to one walking condition based on at least one stored torque pattern corresponding to at least one other walking condition, according to an example embodiment.

In operation 1210, the storage 130 stores a first torque pattern corresponding to each walking condition including, for example, at least one of a walking motion and a walking speed. The first torque pattern may be set differently for each joint used for walking, and set to correspond to each walking condition including, for example, at least one of the walking motion and the walking speed. The a first torque pattern corresponding to each walking condition may be stored in the storage 130.

In operation 1220, the setter 140 sets an unstored first torque pattern based on the stored first torque pattern. In cases that a first torque pattern(s) is/are not stored in the torque pattern adjustment apparatus, the setter 140 may automatically set the unstored first torque pattern based on the first torque pattern stored in the storage 130. A user may directly set the unstored first torque pattern for each walking condition.

The setter 140 may set a first torque pattern corresponding to a third walking condition based on a first torque pattern corresponding to a first walking condition and a first torque pattern corresponding to a second walking condition. In this example, the first torque pattern corresponding to the third walking condition may be a first torque pattern not stored in the storage 130.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of examples have been described above. Nevertheless, it should be understood that various modifications may be made. For example, suitable results may be achieved if the described features are performed in a different order and/or if components in a described system, architecture, device, or circuit are combined in a different manner and/or replaced or supplemented by other components or their equivalents. Accordingly, other implementations are within the scope of the following claims.

What is claimed is:
1. An electronic device including,
a touch screen; and
at least one processor configured to,
display, on the touch screen, a graphical user interface (GUI) screen including a first torque intensity and a second torque intensity for a walking aid device, wherein
the first torque intensity is a torque intensity of a first movement component of a movement of a joint of a user and is displayed on the touch screen as a first number,
the second torque intensity is a torque intensity of a second movement component of the movement of the joint of the user and is displayed on the touch screen as a second number,
the first number is displayed adjacent to a first object associated with the first movement component, and the second number is displayed adjacent to a second object with the second movement component, and the GUI screen is configured to allow the user to touch the first object and the second object to adjust the first torque intensity and the second torque intensity, respectively, receive, via the GUI screen displayed on the touch screen, at least one touch input to adjust at least one of the first torque intensity or the second torque intensity, and provide, to the walking aid device, at least one of the adjusted first torque intensity or the adjusted second torque intensity.

2. The electronic device of claim 1, wherein the at least one processor is further configured to receive, via the GUI screen, the at least one touch input to adjust at least one of an intensity of a peak and a position of the peak for the at least one of the first torque intensity and the second torque intensity.

3. The electronic device of claim 1, wherein the first number and the first object are located on a first region of the GUI screen, and the second number and the second object are located on a second region of the GUI screen, the second region being different from the first region.

4. The electronic device of claim 1, wherein the first number and the second number are numbers represented in percentage values.

5. The electronic device of claim 1, wherein the at least one processor is configured to display on the touch screen,
a first mark indicating a first direction associated with the first torque intensity adjacent to the first object, and
a second mark indicating a second direction associated with the second torque intensity adjacent to the second object.

6. A system for providing walking assistance, comprising:
the electronic device of claim 1; and
a walking aid device including,
at least one processor configured to,
receive, from the electronic device, the adjusted first torque intensity and the adjusted second torque intensity,
set the walking aid device to assist movement of a body part of the user wearing the walking aid device based on the adjusted first torque intensity and the adjusted second torque intensity, the body part being a part associated with the joint, and
apply a first torque corresponding to the adjusted first torque intensity or a second torque corresponding to the adjusted second torque intensity to the body part of the user wearing the walking aid device.

7. A method for controlling a walking assist device, the method comprising:
displaying, on a touch screen of an electronic device, a graphical user interface (GUI) screen including a first torque intensity and a second torque intensity for a walking aid device, wherein
the first torque intensity is a torque intensity of a first movement component of a movement of a joint of a user and is displayed on the touch screen as a first number, and
the second torque intensity is a torque intensity of a second movement component of the movement of the joint of the user and is displayed on the touch screen as a second number,
the first number is displayed adjacent to a first object associated with the first movement component, and the second number is displayed adjacent to a second object with the second movement component, and the GUI screen is configured to allow the user to touch the first object and the second object to adjust the first torque intensity and the second torque intensity, respectively, receiving, via the GUI screen displayed on the touch screen, at least one touch input to adjust at least one of the first torque intensity or the second torque intensity; and providing, to the walking aid device, at least one of the adjusted first torque intensity and the adjusted second torque intensity.

8. The method of claim 7, wherein the at least one touch input is one or more inputs of the user to adjust at least one of an intensity of a peak and a position of the peak for the at least one of the first torque intensity and the second torque intensity.

9. The method of claim 7, wherein the displaying includes displaying the first number and the first object on a first region of the GUI screen, and displaying the second number and the second object on a second region of the GUI screen, the second region being different from the first region.

10. The method of claim 7, wherein the first number and the second number are numbers represented in percentage values.

11. The method of claim 7, wherein the displaying includes,
displaying, on the GUI screen, a first mark indicating a first direction associated with the first torque intensity adjacent to the first object, and
displaying, on the GUI screen, a second mark indicating a second direction associated with the second torque intensity adjacent to the second object.

12. The method of claim 7, further comprising:
receiving, by a walking assist device from the electronic device, the adjusted first torque intensity and the adjusted second torque intensity;
setting the walking aid device to assist movement of a body part of the user wearing the walking aid device based on the adjusted first torque intensity and the adjusted second torque intensity, the body part being a part associated with the joint; and
apply a first torque corresponding to the adjusted first torque intensity or a second torque corresponding to the adjusted second torque intensity to the body part of the user wearing the walking aid device.

13. A non-transitory computer-readable recording medium storing instructions that, when executed by a processor, cause the processor to perform the method of claim 7.

14. A walking aid device comprising:
a processor configured to,
receive, from an electronic device, at least one of an adjusted first torque intensity and an adjusted second torque intensity,
set the walking aid device to assist movement of a leg of a user wearing the walking aid device based on at least one of the adjusted first torque intensity and the adjusted second torque intensity, and
apply a first torque corresponding to the adjusted first torque intensity or a second torque corresponding to the adjusted second torque intensity to the leg of the user wearing the walking aid device, wherein
the at least one of the adjusted first torque intensity and the adjusted second torque intensity is determined via a graphical user interface (GUI) screen of the electronic device, the GUI screen is configured to allow the user to adjust a first torque intensity and a second torque intensity based on at least one touch input of the user to a first object and a second object, respectively, the first torque intensity is a torque intensity of a first movement component of a movement of a joint of the user and is displayed on the GUI screen as a first number, the second torque intensity is a torque intensity of a second movement component of the movement of the joint of the user and is displayed on the GUI screen as a second number, and the first number is displayed adjacent to the first object associated with the first movement component, and the second number is displayed adjacent to the second object with the second movement component.

15. The walking aid device of claim 14, wherein the at least one touch input is one or more inputs of the user to adjust at least one of an intensity of a peak and a position of the peak for the at least one of the first torque intensity and the second torque intensity.

16. The walking aid device of claim 14, wherein the first number and the first object are displayed on a first region of the GUI screen, and the second number and the second object are displayed on a second region of the GUI screen, the second region being different from the first region.

17. The walking aid device of claim 14, wherein the first number and the second number are numbers represented in percentage values.

18. The walking aid device of claim 14, wherein the processor is further configured to, receive, from the electronic device, the adjusted first torque intensity and the adjusted second torque intensity, set the walking aid device to assist movement of the leg of the user wearing the walking aid device based on the adjusted first torque intensity and the adjusted second torque intensity, and apply a first torque corresponding to the adjusted first torque intensity or a second torque corresponding to the adjusted second torque intensity to the leg of the user wearing the walking aid device.

* * * * *